United States Patent [19]

Cimarusti

[11] 3,945,997
[45] Mar. 23, 1976

[54] STEROIDAL BICYCLIC DIOXANES
[75] Inventor: Christopher M. Cimarusti, Hamilton, N.J.
[73] Assignee: E. R. Squibb & Sons, Inc., Princeton, N.J.
[22] Filed: May 19, 1975
[21] Appl. No.: 578,597

[52] U.S. Cl..... 260/239.55 R; 424/241; 260/397.45
[51] Int. Cl.² ............................................ C07J 71/00
[58] Field of Search .......................... 260/239.55 R

[56] References Cited
UNITED STATES PATENTS
3,905,962  9/1975  Marx et al. .................. 260/239.55 R Primary Examiner—Elbert L. Roberts
Attorney, Agent, or Firm—Lawrence S. Levinson; Merle J. Smith; Donald J. Barrack

[57] ABSTRACT
Steroids having the structure

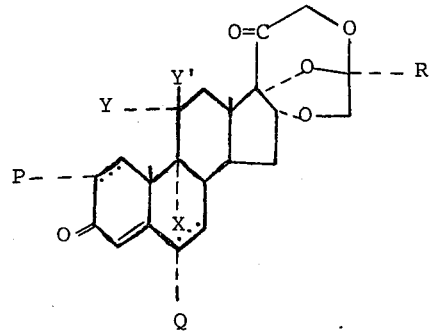

wherein P is hydrogen, methyl or chloro; Q is hydrogen, methyl or fluoro; X is hydrogen or halogen; Y is hydrogen and Y' is hydroxyl or together Y and Y' can be =O; and R can be hydrogen, alkyl or aryl; have useful anti-inflammatory activity.

13 Claims, No Drawings

STEROIDAL BICYCLIC DIOXANES

SUMMARY OF THE INVENTION

Steroids having the structure

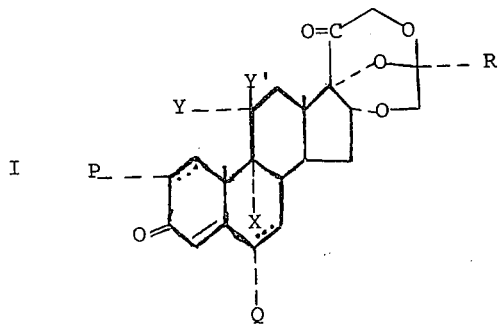

are useful anti-inflammatory agents. In formula I, and throughout the specification, the symbols are as defined below.

P can be hydrogen, methyl or chloro;
Q can be hydrogen, methyl or fluoro;
X can be hydrogen or halogen;
Y can be hydrogen and Y' can be hydroxyl, or together Y and Y' can be =O; and
R can be hydrogen, alkyl or aryl.

The dotted lines in the 1,2- and 6,7-positions of the steroids of this invention represent the optional presence of double bonds.

The term "alkyl", as used throughout the specification, refers to both branched and straight chain alkyl groups having 1 to 8 carbon atoms. Alkyl groups of 1 to 4 carbon atoms are preferred, and methyl is the most preferred.

The term "aryl", as used throughout the specification, refers to phenyl or phenyl substituted with one or more halogen, alkyl, and alkoxy groups. Phenyl and monosubstituted phenyl are the preferred aryl groups.

The term "halogen", as used throughout the specification, refers to fluorine, chlorine, bromine, and iodine.

The term "alkoxy", as used throughout the specification, refers to groups having the structure alkyl-O- wherein alkyl is a defined above. Alkoxy groups having 1 to 4 carbon atoms are preferred, and methoxy is the most preferred.

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion. The topical mode of administration is preferred.

The novel steroids of this invention can be prepared from steroidal [16α, 17-b] dioxins having the structure

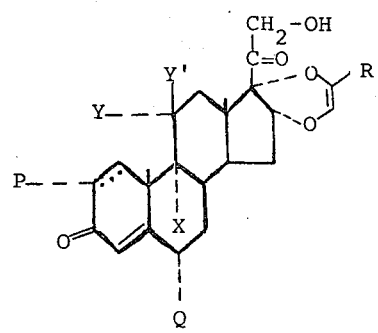

A steroid of formula II can be reacted in a slurry or solution of an organic acid catalyst, e.g., p-toluenesulfonic acid, in an organic solvent, e.g., benzene, to yield the corresponding steroid of formula I. The reaction can be conducted under reflux conditions in an inert atmosphere for about 2 to 48 hours, preferably 4 to 24 hours.

Starting steroids of formula II are prepared by first reacting a cycloborate ester having the formula

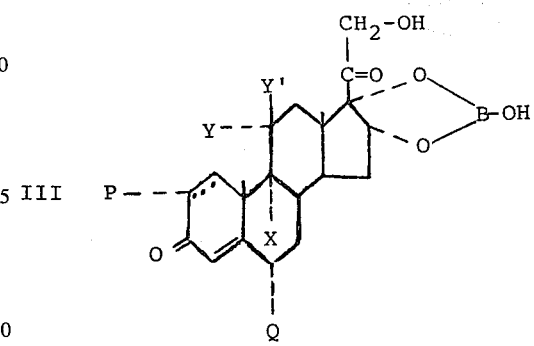

with a diazoalkene having the formula

IV
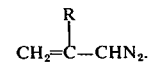

The cycloborate esters of formula III can be prepared by reacting the corresponding 16α,17-dihydroxy steroid with boric acid anhydride in an organic solvent at reflux temperature. The diazoalkenes of formula IV wherein R is hydrogen or alkyl are known; see, for example, the *Journal of the American Chemical Society*, 91, 711 (1969). The preparation of a diazoalkene of formula IV wherein R is aryl is described in the examples of this specification.

Reaction of a cycloborate ester of formula III with a diazoalkene of formula IV yields a steroid having the formula

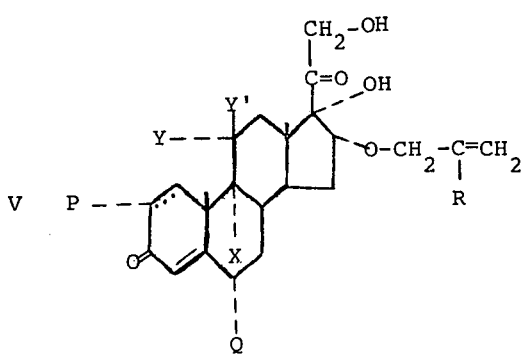

The reaction can be conducted in an organic solvent, preferably a lower alkanol such as methanol, at a temperature of about −10°C to +40°C for about 30 minutes to 4 hours, preferably at 0°C to 20°C for 30 minutes to 1 hour. The steroid and the diazoalkene are reacted in at least a 1:4 molar ratio.

A steroid of formula V can be reacted with an acid anhydride or acid halide of the formula $(R'CO)_2O$ or

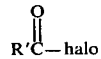

(wherein R' is alkyl or aryl) to give a protected steroid having the formula

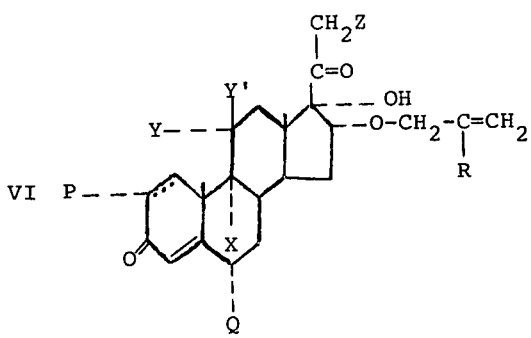

wherein Z is

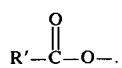

The reaction can be conducted in organic solvent in the presence of a weak base, preferably in a solvent such as pyridine which also acts as the base.

Alternatively, a cycloborate ester having the formula

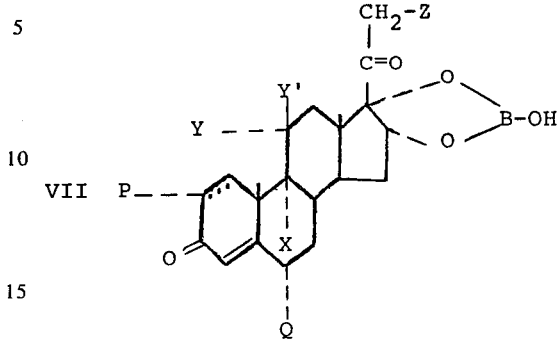

can be reacted with a diazoalkene of formula IV to yield a steroid of formula VI.

A steroid of formula VI can be reacted with m-chloroperbenzoic acid to yield a steroid having the formula

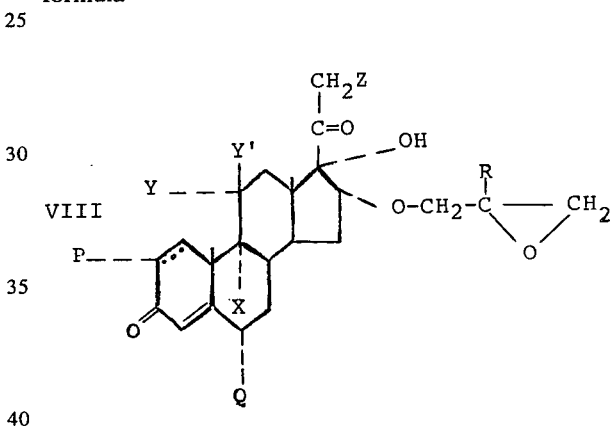

The reaction can be conducted in an organic solvent, preferably a halogenated hydrocarbon such as dichloromethane, at a temperature of from about 0°C to 40°C for about 1 hour to 96 hours, preferably at room temperature for about 2 hours to 72 hours. A steroid of formula VI and m-chloroperbenzoic acid are reacted in approximately a 1:1 molar ratio.

Reaction of a steroid of formula VIII when R is alkyl or aryl with a strong oxidizing agent, e.g., periodic acid, yields a steroid having the formula

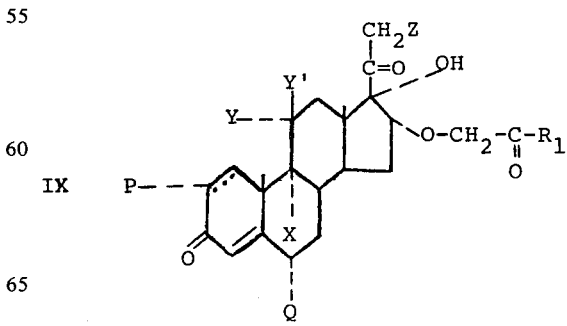

wherein $R_1$ can be alkyl, or aryl. Reaction of a steroid of formula VIII when R is hydrogen with a strong oxidizing agent yields a cyclic lactol (formula X) which is in equilibrium with the corresponding aldehyde (formula Xa), i.e.,

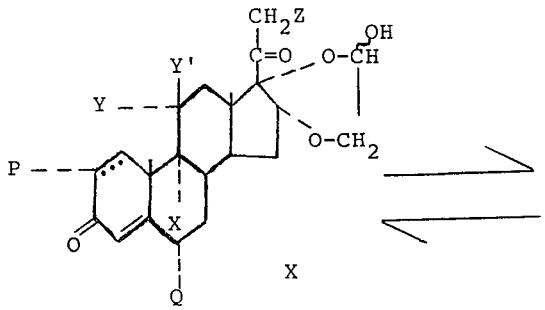 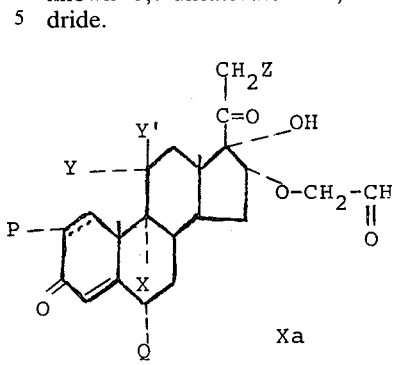

These oxidation reactions can be conducted in an organic solvent such as tetrahydrofuran mixed with water at a temperature of about 0°C to 40°C, for about 1 hour to 8 hours, preferably at room temperature for 2 hours to 4 hours.

The steroids of formula IX and X can be reacted in a slurry or solution of an organic acid catalyst such as p-toluenesulfonic acid in an organic solvent such as benzene to yield steroidal 2',3'-dihydro[16α,17-b]1,4-dioxins having the formula

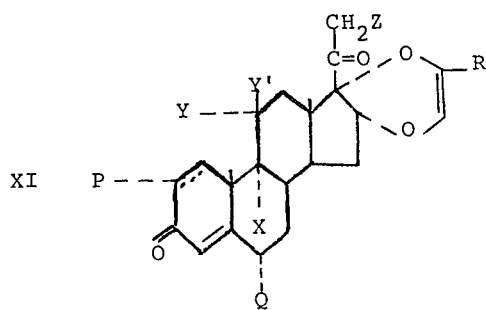

The reaction can be conducted under reflux conditions in an inert atmosphere for about 2 hours to 48 hours, preferably 4 hours to 24 hours.

Saponification of a steroidal 2',3'-dihydro[16α,17-b]1,4-dioxin of formula XI, using conventional techniques, yields the corresponding 21-hydroxy steroids of formula II.

Those steroids of formula I containing ethylenic unsaturation in the 6,7-position can be prepared as described above with the additional step of selectively introducing a carbon-carbon double bond in the 6,7-position of either a steroid starting material of formula III or VII or a steroid product of formula I without effecting other functional groups of the steroid. Exemplary of the oxidizing agents which meet the above requirements is 2,3-dichloro-5,6-dicyano-1,4-benzoquinone when used in the presence of an acid. About one molar equivalent of the oxidizing agent is used per molar equivalent of steroid. The oxidation reaction can be conducted in an organic solvent such as benzene, toluene, dioxane, etc.; dioxane is preferred. The reaction can be carried out for about 1 hour to 96 hours at a temperature of about 50°C to 150°C, preferably for about 4 to 24 hours at about 70°C to 130°C. Alternately a cycloborate containing unsaturation in the 6,7-position can be prepared from the corresponding, known 6,7-unsaturated 16,17-diols and boric anhydride.

Additional methods for the preparation of the compounds of this invention will be readily apparent to a person of ordinary skill in the steroid art.

The following examples are specific embodiments of this invention.

EXAMPLE 1

9-Fluoro-11β-hydroxy-1'α-methylandrost-4-eno[17β,16α-e]-[2,7,9]trioxabicyclo[3.3.1]nonane-3,4'-dione A.
9-Fluoro-11β,17,21-trihydroxy-16α-[(2-methyl-2-propenyl)oxy]pregn-4-ene-3,20-dione A solution of 2-methyl-3-diazo-1-propene in 250 ml of ether (prepared from 0.2 mole of N-(2-methyl-2-propenyl)ethyl carbamate by the method of J. L. Brewbaker and H. Hart, J. Am. Chem. Soc., 91, 711 (1969) is diluted with 300 ml of methanol and cooled to 0°C. A total of 6.5 g of 9-fluoro-11β,16α,17,21-tetrahydroxypregn-4-ene-3,20-dione,16,17-cycloborate is added in portions until the initial red color fades and nitrogen evolution ceases. The solvent is evaporated in vacuo and the residue dissolved in chloroform and chromatographed on a 100 g - silica gel column. Elution with chloroform and chloroform-ethyl acetate gives TLC homogeneous material which crystallizes from acetone-hexane to give 3.73 g of 9-fluoro-11β,17,21-trihydroxy-16α-[(2-methyl-2-propenyl)oxy]pregn-4-ene-3,20-dione, melting point 213°–215°C, softening at 198°–200°C.

B. 9-Fluoro-11β,17,21-trihydroxy-16α-[(2-methyl-2-propenyl)oxy]pregn-4-ene-3,20-dione, 21-acetate A solution of 3 g of 9-fluoro-11β,17,21-trihydroxy-16α-[(2-methyl-2-propenyl)oxy]pregn-4-ene-3,20-dione in 25 ml of pyridine is stirred for 2 hours with 4 ml of acetic anhydride. The solvent is removed in vacuo and the residue is dissolved in chloroform, washed with 5% hydrochloric acid solution, water, 5% sodium bicarbonate solution, and dried. Solvent removal in vacuo gives a solid which is recrystallized from acetone-hexane to give 2.82 g of material having a melting point of 230°–231°C. Recrystallization of 0.6 g of this material from acetone-hexane gives 481 mg of 9-fluoro-11β,17,21-trihydroxy-16α-[(2-methyl-2-propenyl)oxy]pregn-4-ene-3,20-dione, 21-acetate, melting point 230°–232°C.

C.
9-Fluoro-11β,17,21-trihydroxy-16α-[(2-methyl-oxiranyl)methoxy]pregn-4-ene-3,20-dione, 21-acetate A slurry of 1.0 g of 9-fluoro-11β,17,21-trihydroxy-16α-[(2-methyl-2-propenyl)oxy]pregn-4-ene-3,20-dione, 21-acetate in 50 ml of dichloromethane is stirred with 500 mg of m-chloroperbenzoic acid at room temperature for 210 minutes. The resulting solution is washed with a mixture of 10% sodium carbonate solution and 10% sodium sulfite solution, dried, and evaporated to give 1.04 g of oil which solidifies. Recrystallization from acetone-hexane gives 793 mg of material, melting point 221°–224°C and 160 mg of material, melting point 219°–224°C. Recrystallization of a mixture of 390 mg of crop 1 and 160 mg of crop 2 from acetone-hexane gives 298 mg of 9-fluoro-11β,17,21-trihydroxy-16α-[(2-methyl-oxiranyl)methoxy]pregn-4-ene-3,20-dione, 21-acetate, melting point 223°–227°C.

Anal. Calc'd for $C_{27}H_{37}FO_8$: C, 63.76; H, 7.33; F, 3.74. Found: C, 63.96; H, 7.10; F, 3.93.

The nmr spectrum of this material indicates it is a mixture of epimers (ca. 2:1 ratio) at the quaternary epoxide carbon atom.

D.
9-Fluoro-11β,17,21-trihydroxy-16α-(2-oxopropoxy)-pregn-4-ene-3,20-dione, 21-acetate A solution of 1.54 g of 9-fluoro-11β,17,21-trihydroxy-16α-[(2-methyl-oxiranyl)methoxy]pregn-4-ene-3,20-dione, 21-acetate in 50 ml of tetrahydrofuran is stirred for 270 minutes with a solution of 2.6 g of periodic acid in 20 ml of water. The solution is poured into water and extracted with chloroform. The chloroform solution is washed with 10% sodium bicarbonate solution, dried, and evaporated in vacuo to give an oily residue. This is dissolved in chloroform and chromatographed on a 40 g-silica gel column. Elution with chloroform gives 400 mg of slightly impure product followed by 990 mg of TLC homogeneous solid. The 990 mg is recrystallized twice from acetone-hexane to give 328 mg of 9-fluoro-11β,17,21-trihydroxy-16α-(2-oxopropoxy)pregn-4-ene-3,20-dione, 21-acetate, melting point 203°–208°C.

E.
9-Fluoro-2',3'-dihydro-11β,21-dihydroxy-5'-methylpregn-4-eno[16α,17-b][1,4]dioxin-3,20-dione, 21-acetate A slurry of 100 mg of p-toluenesulfonic acid in 250 ml of benzene is refluxed with a Dean-Stark trap. The first 50 ml of benzene-water azeotrope is discarded and Linde type 4A molecular sieves are added to the trap. After 30 minutes at reflux, the solution is cooled and 1.0 g of 9-fluoro-11β,17,21-trihydroxy-16α-(2-oxopropoxy)pregn-4-ene-3,20-dione, 21-acetate is added. The resulting slurry is refluxed for 5 hours under nitrogen, cooled, diluted with chloroform, washed with 5% sodium bicarbonate solution, water, dried and evaporated. The crude residue is dissolved in a small amount of chloroform and chromatographed on a 20 g - silica gel column. Elution with chloroform gives 805 mg of material which is recrystallized from -acetone-hexane to give 501 mg of 9-fluoro-2',3'-dihydro-11β,21-dihydroxy-5'-methylpregn-4-eno[16α,17-b][1,4]dioxin-3,20-dione, 21-acetate, melting point 233°–235°C, dec.

F.
9-Fluoro-2',3'-dihydro-11β,21-dihydroxy-5'-methylpregn-4-eno[16α,17-b][1,4]dioxin-3,20-dione A solution of 886 mg of 9-fluoro-2',3'-dihydro-11β,21-dihydroxy-5'-methylpregn-4-eno[16α,17-b][1,4]dioxin-3,20-dione, 21-acetate in 270 ml of methanol is cooled to 0°C and 27 ml of 10% potassium carbonate solution is added. After 15 minutes, 27 ml of acetic acid is added and the mixture is diluted with water and extracted with chloroform to give 775 mg of TLC pure 9-fluoro-2',3'-dihydro-11β,21-dihydroxy-5'-methylpregn-4-eno[16α,17-b][1,4]dioxin-3,20-dione.

G.
9-Fluoro-11β-hydroxy-1'α-methylandrost-4-eno[17β,16α-e][2,7,9]trioxabicyclo[3.3.1]nonane-3,4'-dione A slurry of 150 mg of p-toluenesulfonic acid in 600 ml of benzene is refluxed with a Dean-Stark trap. The first 100 ml was discarded, Linde 4A molecular sieves are added to the trap, and the solution is refluxed for 30 minutes. The solution is cooled and 755 mg of 9-fluoro-2',3'-dihydro-11β,21-dihydroxy-5'-methylpregn-4-eno[16α,17-b][1,4]dioxin-3,20-dione is added. The resulting slurry is refluxed for 1 hour and the benzene is evaporated in vacuo. The residue is dissolved in chloroform, washed with 5% sodium bicarbonate solution, water, dried and evaporated in vacuo. The residue is dissolved in chloroform and chromatographed on a 40 g - silica gel column. Elution with chloroform gives 580 mg of material that is recrystallized twice from -acetone-hexane to give 375 mg of 9-fluoro-11β-hydroxy-1'α-methylandroust-4-eno[17β,16α-e][2,7,9]trioxabicyclo[3.3.1]nonane-3,4' -dione, melting point 248°–250°C, dec.

Anal. Calc'd. for $C_{24}H_{31}FO_6$: C, 66.34; H, 7.19; F, 4.37. Found: C, 66.06; H, 7.18; F, 4.18.

EXAMPLE 2

9-Fluoro-11β-hydroxy-1'α-phenylandrost-4-eno[17β,16α-e][2,7,9]trioxabicyclo[3.3.1]nonane-3,4'-dione

A.
9-fluoro-11β,17,21-trihydroxy-16α-[(2-phenyl-2-propenyl)oxy]pregn-4-ene-3,20-dione, 21-acetate a. N-(2-phenyl-2-propenyl)phthalimide A mixture of 60 g of potassium phthalimide and 66.4 g of α-bromomethyl styrene (prepared by the method of S. F. Reed, Jr., *J. Org. Chem.*, 30, 3258 (1965)) in 150 ml of dimethylformamide is refluxed for 2 hours, cooled, and diluted with 400 ml of water. The resulting solid is filtered and dried in vacuo to give 83.4 g of N-(2-phenyl-2-propenyl)phthalimide. A small sample that is recrystallized from acetone-hexane has a melting point of 118°–121°C.

b. N-(2-phenyl-2-propenyl)ethyl carbamate

A solution of 83 g of N-(2-phenyl-2-propenyl)phthalimide and 30 g of 99% hydrazine-hydrate is refluxed for 270 minutes and cooled. The slurry is treated with 125 ml of conc. hydrochloric acid and filtered. The solid is washed with four 100 ml portions of water and the filtrate is evaporated in vacuo to a volume of 300 ml. This solution is cooled and mixed with a solution of 60 g of sodium hydroxide in 250 ml of cold water. The resulting solution is extracted with four 200 ml portions of ether and the ether solution is dried and evaporated in vacuo to give 30.7 g of oil. The oil is dissolved in 250 ml of ether, cooled to 0°C, and 33 g of ethyl chloroformate is added. A solution of 12 g of sodium hydroxide in 30 ml of water is added simultaneously with the second half of the ethyl chloroformate solution. After 1 hour at 10°C, the ether layer is washed with 5% hydrochloric acid, dried, and evaporated in vacuo to give 41.7 g of oil. Trituration with hexane and filtration gave 33 g of N-(2-phenyl-2-propenyl)ethyl carbamate, melting point 41°–42.5°C.

c. N-Nitroso-N-(2-phenyl-2-propenyl)ethyl carbamate

A solution of 21 ml (29.4 g) of nitrosyl chloride in 60 ml of pyridine (prepared at −25°C) is added over a period of 15 minutes to a solution of 57 g of N-(2-phenyl-2-propenyl)ethyl carbamate in 400 ml of pyridine at −5°C. The solution is stirred for 15 minutes and poured into 4 liters of cold water. The oil which separates is extracted into ether (three 600 ml portions) and the ether extract is washed successively with 1 liter of 10% hydrochloric acid, water, 1 liter of 5% sodium bicarbonate solution, and dried. Solvent removal gives 63 g of red oil that shows only minor impurities on TLC.

d. 2-Phenyl-3-diazo-1-propene

A solution of 63 g of N-nitroso-N-(2-phenyl-2-propenyl)ethyl carbamate in 300 N-nitroso-n-(ml of ether is added to 300 ml of 3M sodium methoxide in methanol at −1° to −2°C over a period of 30 minutes. The solution is stirred for a further hour and then poured into 2 liters of ice water and 100 ml each of ether and pentane. The organic layer is separated and kept at 0°C while the aqueous layer is extracted with 300 ml of ether. The combined organic layer is washed with two 1 liter portions of ice water, dried for 10 minutes at 0°C over NaOH pellets, and filtered to give 700 ml of red solution.

e.
9-Fluoro-11β,17,21-trihydroxy-16α-[(2-phenyl-2-propenyl)oxy]pregn-4-ene-3,20-dione The solution of 2-phenyl-3-diazo-1-propene prepared as described above is diluted with 150 ml of cold methanol and stirred well at 0°C as 13 g of 9-fluoro-11β,16α,17,21-tetrahydroxypregn-4-ene-3,20-dione, 16,17-cycloborate is added in portions. The slurry is stirred for 1 hour at 0°C and filtered to give 9.6 g of the title compound. The filtrate is stirred at room temperature for 1 hour with 4 g of the cycloborate and the resulting solution is cooled to 0°C and filtered to give 4.2 g of the title compound. The filtrate is evaporated in vacuo and the residue is dissolved in 400 ml of 3:1 ether-methanol and cooled to −10°C to give a further 3.0 g of material. A small sample recrystallized from acetone-hexane has a melting point of 161°–163.5°C.

B.
9-Fluoro-11β,17,21-trihydroxy-16α-[(2-phenyl-2-propenyl)oxy]pregn-4-ene-3,20-dione, 21-acetate A solution of 3.0 g of 9-fluoro-11β,17,21-trihydroxy-16α-[(2-phenyl-2-propenyl)oxy]pregn-4-ene-3,20-dione in 30 ml of pyridine is allowed to stand with 3 ml of acetic anhydride for 2 hours at room temperature. The solvent is removed in vacuo and the residue is dissolved in chloroform, washed with 5% hydrochloric acid, water, 5% sodium bicarbonate solution, and dried. Solvent removal gives an oil that crystallizes from acetone-hexane to give 2.3 g of material. Recrystallization of 600 mg from acetone-hexane gives 510 mg of 9-fluoro-11β,17,21-trihydroxy-16α-[(2-phenyl-2-propenyl)oxy]pregn-4-ene-3,20-dione, 21-acetate, melting point 169°–171°C.

C.
9-Fluoro-11β,17,21-trihydroxy-16α-[(2-phenyloxiranyl)methoxy]pregn-4-ene-3,20-dione 21-acetate A solution of 555 mg of 9-fluoro-11β,17,21-trihydroxy-16α-[(2-phenyl-2-propenyl)oxy]pregn-4-ene-3,20-dione, 21-acetate in 25 ml of dichloromethane is stirred for 330 minutes with 200 mg of m-chloroperbenzoic acid. The solution is washed with 50 ml each of 5% sodium sulfite solution and 5% potassium carbonate solution. The dichloromethane solution is dried and evaporated to give 582 mg of product. Recrystallization from acetone-hexane gives 360 mg of 9-fluoro-11β,17,21-trihydroxy-16α-[(2-phenyloxiranyl)methoxy]pregn-4-ene-3,20-dione, 21-acetate.

D.
9-Fluoro-11β,17,21-trihydroxy-16α-(2-phenyl-2-oxoethoxy)pregn-4-ene-3,20-dione, 21-acetate A solution of 2.4 g of 9-fluoro-11β,17,21-trihydroxy-16α-[(2-phenyl-oxiranyl)methoxy]pregn-4-ene-3,20-dione, 21-acetate in 75 ml of tetrahydrofuran is stirred with a solution of 5 g of periodic acid in 20 ml of water for 270 minutes. The resulting slurry is diluted with 150 ml of water and the solid is filtered and dried in vacuo to give 1.79 g of crude product. This material is chromatographed on a 40 g-silica gel column. Elution with chloroform gives 1.6 g of TLC pure solid that is recrystallized from acetone-hexane to give 1.42 g of 9-fluoro-11β,17,21-trihydroxy-16α-(2-phenyl-2-oxoethoxy)-pregn-4-ene-3,20-dione, 21-acetate, melting point 228°–230°C.

E.
9-Fluoro-2',3'-dihydro-11β,21-dihydroxy-5'-phenylpregn-4-eno[16α,17-b][1,4]dioxin-3,20-dione, 21-acetate A slurry of 150 mg of p-toluenesulfonic acid in 300 ml of benzene is refluxed with a Dean-Stark trap. The first 50 ml of distillate is discarded, Linde 4A molecular sieves added, and the solution is refluxed for 30 minutes. The solution is cooled, 1.25 g of 9-fluoro-11β,17,21-trihydroxy-16α-(2-phenyl-2-oxoethoxy)-pregn-4-ene-3,20-dione, 21-acetate added, and the solution refluxed for 5 hours under nitrogen. The resulting solution is cooled, washed with 5% sodium bicarbonate solution, dried, and evaporated in vacuo. The residue is chromatographed on a 20 g-silica gel column. Elution with 1:1 hexane-chloroform gives 825 mg of crude product. This material is plate chromatographed on three 20 × 20 cm-2mm silica gel plates. After 2 developments with 1:1 chloroform-ethyl acetate the major UV-active band is excised and eluted with chloroform to give TLC pure material. Recrystallization from benzene gives 380 mg of 9-fluoro-2',3'-dihydro-11β,21-dihydroxy-5'-phenylpregm-4-eno[1-6α,17-b][1,4]dioxin-3,20-dione, 21-acetate, melting point 145°–147°C.

F.
9-Fluoro-11β,21-dihydroxy-2',3'-dihydro-5'-phenylpregn-4-eno[16α,17-b],4]dioxin-3,20-dione A solution of 1.89 g of 9-fluoro-2',3'-dihydro-11β,21-dihydroxy-5'-phenylpregn-4-eno[16α,17-b][1,4]dioxin-3,20-dione, 21-acetate in 100 ml of methanol is cooled to 0°C under nitrogen and 10 ml of 10% potassium carbonate solution is added. After 75 minutes, 10 ml of glacial acetic acid is added and the solution is diluted with water and extracted with chloroform. The chloroform solution is dried and evaporated in vacuo to give 1.65 g of crude product. This is dissolved in chloroform and chromatographed on a 40 g-silica gel column. Elution with chloroform and then 1:1 chloroform-ethyl acetate gives 1.48 g of 9-fluoro-11β,21-dihydroxy-2′,3′-dihydro-5′-phenylpregn-4-eno[16α,17-b][1,4]dioxin-3,20-dione.

G.
9-Fluoro-11β-hydroxy-1′α-phenylandrost-4-eno[17β,16α-e][2,7,9]trioxabicyclo[3.3.1]nonane-3,4′-dione A slurry of 150 mg of p-toluenesulfonic acid in 300 ml of benzene is distilled to a volume of 250 ml, cooled and 1.48 g of 9-fluoro-11β,21-dihydroxy-2′,3′-dihydro-5′-phenylpregn-4-eno[16α,17-b][1,4]dioxin-3,20-dione is added. The resulting solution is refluxed for 2 hours under nitrogen, cooled, washed with 5% sodium bicarbonate solution, and dried. Solvent removal gives an oil which is dissolved in chloroform and chromatographed on a 40 g-silica gel column. Elution with chloroform gives 260 mg of slightly impure material which is plate-chromatographed on a 20 × 20 cm-2mm silica gel plate developed twice with 1:1 chloroform-ethyl acetate. The major UV-active band is excised and eluted with ethyl acetate to give 205 mg of material. Recrystallization from methanol gives 110 mg, melting point 250°–252°C, dec. This material is combined with 88 mg of similar material from another run and purified further by the sequence of plate chromatography, crystallization from acetone-hexane, plate chromatography, and a final recrystallization from acetone-hexane to give 80 mg of 9-fluoro-11β-hydroxy-1′α-phenylandrost-4-eno]17β,16α-e][2,7,9]trioxabicyclo[3.3.1]nonane-3,4′-dione, melting point 238°–240°C.

Anal. Calc'd. for $C_{29}H_{33}FO_6$: C, 70.14; H, 6.70; F, 3.83; Found: C, 70.40; H, 6.78; F, 3.68

EXAMPLE 3
9-Fluoro-11β-hydroxyandrost-4-eno[17β,16α-e][2,7,9]trioxabicyclo[3.3.1]nonane-3,4′-dione

A.
16α-Allyloxy-9-fluoro-11β,17,21-trihydroxypregn-4-ene-3,20-dione 6.6 g of 9-fluoro-11β,16α,17,21-tetrahydropregn-4-ene-3,20-dione,16,17-cycloborate is added to a solution of vinyl diazomethane in 1:1 methanol-ether at 0°C. After stirring for 1 hour, the solvent is evaporated and the residue dissolved in chloroform and chromatographed on a 150-g silica gel column. Elution with 5% ethyl acetate in chloroform gives 1.04 g of TLC (thin layer chromatography) pure material. Two recrystallizations from acetone-hexane give 0.5 g of 16α-allyloxy-9-fluoro-11β,17,21-trihydroxypregn-4-ene-3,20-dione, melting point 199°–201°C.

B.
16α-Allyloxy-9-fluoro-11β,17,21-trihydroxypregn-4-ene-3,20-dione, 21-acetate A solution of 2.5 g of 16α-allyloxy-9-fluoro-11β,17,21-trihydroxypregn-4-ene-3,20-dione in 25 ml of pyridine is stirred for 2 hours with 2.5 ml of acetic anhydride and the solvent is then removed in vacuo. A solution of the residue is chloroform is washed with 5% hydrochloric acid, water, 10% sodium bicarbonate solution, water, and dried. Solvent removal in vacuo gives an oil which crystallizes from acetone-hexane to yield 2.5 g of 16α-allyloxy-9-fluoro-11β,17,21-trihydroxypregn-4-ene-3,20-dione, 21-acetate, melting point 189°–191°C.

C.
9-Fluoro-11β,17,21-trihydroxy-16α-(oxiranyl-methoxy)-pregn-4-ene-3,20-dione, 21-acetate A solution of 6.44 g of 16α-allyloxy-9-fluoro-11β,17,21-trihydroxypregn-4-ene-3,20-dione, 21-acetate in 150 ml of dichloromethane is stirred with 2.88 g of m-chloroperbenzoic acid for 19 hours at room temperature. The resulting solution is washed with a mixture of 10% potassium carbonate solution and 10% sodium sulfite solution, dried, and evaporated in vacuo. The residue is dissolved in dichloromethane and chromatographed on a 125 g - silica gel column. Elution with chloroform and a chloroform-ethyl acetate mixture gives 3.5 g of unreacted starting material in fractions (100 ml) 25–37 and 1.7 g (25.6%) of TLC pure product in fractions 49–61.

The 1.7 g is recrystallized from acetone-hexane to give 991 mg of material having a melting point of 191°–192.5°C. A 500 mg portion of this material is recrystallized from the same solvent to give 430 mg of 9-fluoro-11β,17,21-trihydroxy-16α-(oxiranyl-methoxy)pregn-4-ene-3,20-dione, 21-acetate, melting point 191°–192.5°C.

D.
9-Fluoro-5′ξ,11β,21-trihydroxypregn-4-eno[16α,17-b]-[1,4]dioxane-3,20-dione, 21-acetate A solution of 20.1 g of crude 9-fluoro-11β,17,21-trihydroxy-16α-(oxiranyl-methoxy)pregn-4-ene-3,20-dione, 21-acetate in 300 ml of tetrahydrofuran is stirred with a solution of 30 g of periodic acid in 75 ml of water for 6 3/4 hours. The solution is diluted with water and extracted with chloroform. The chloroform extract was washed with 5% sodium bicarbonate solution, dried, and evaporated in vacuo to give 18.2 g of crude product. This material is dissolved in 60 ml of dichloromethane and chromatographed on a 450 g-silica gel column. Fractions of 250 ml are collected as the column is eluted with 3 liters of dichloromethane, 3 liters of chloroform, and then 3 liters of 19:1 chloroform-ethyl acetate. Fractions 17–21 are combined and evaporated in vacuo to give 4.4 g of 16α-allyloxy-9-fluoro-11β,17,21-trihydroxypregn-4-ene-3,20-dione, 21-acetate.

Fractions 23–31 are combined and evaporated in vacuo to give 8.1 g of slightly impure (53.2% based on recovered material) 9-fluoro-5′ξ,11β,21-trihydroxypregn-4-eno[16α,17-b][1,4]dioxane-3,20-dione, 21-acetate. A portion of this material is recrystallized from acetone-hexane and then from acetonitrile to give the analytical sample, melting point 205°–208°C.

E.
9-Fluoro-2′,3′-dihydro-11β,21-dihydroxypregn-4-eno[16α,17-b][1,4]dioxin-3,20-dione, 21-acetate A -fluoro-of 100 mg of p-toluenesulfonic acid in 250 ml of benzene is distilled to a volume of 200 ml and 1.0 g of 9-fluoro15′ξ,11β,21-trihydroxypregn-4-eno]16α,17-b][1,4]dioxane-3,20-dione, 21-acetate is added. The resulting solution is refluxed with a Dean-Stark trap filled with 4A molecular sieves for 24 hours under nitrogen. The solution is cooled, diluted with chloroform, washed with 5% sodium bicarbonate solution, and dried. The residue obtained on solvent removal in vacuo is chromatographed on a 20 g-silica gel column. Elution with 1:1 dichloromethane-chloroform gives 510 mg of pure compound. Recrystallization from acetone-hexane gives 325 mg of TLC pure solid, in two crops. The mother liquor is purified by preparative thin layer chromatography on a 20 X 20 cm2 mm silica gel plate. After three developments with 9:1 chloroform-ethyl acetate, the major UV-active band is excised and eluted with chloroform-methanol. The residue obtained on solvent removal is crystallized from acetone-hexane to give 96 mg of pure material. This is combined with the 325 mg obtained above and recrystallized from acetone-hexane to give 312 mg of 9-fluoro-2',3'-dihydro-11β,21-dihydroxypregn-4-eno[16α,17-b][1,4]dioxin-3,20-dione, 21-acetate, melting point 231°–240°C, dec.

F.
9-Fluoro-2',3'-dihydro-11β,21-dihydroxypregn-4-eno[16α,17-b][1,4]dioxin-3,20-dione A solution of 700 mg of 9-fluoro-2',3'-dihydro-11β,21-dihydroxypregn-4-eno[16α,17-b][1,4]-dioxin-3,20-dione, 21-acetate on 75 ml of methanol is cooled to 0°C and 7 ml of 10% potassium carbonate solution is added. After 15 minutes, 20 ml of 20% aqueous acetic acid is added and the resulting solid is filtered and dried in vacuo to give 310 mg of 9-fluoro-2',3'-dihydro-11β,21-dihydroxypregn-4-eno[16α,17-b][1,4]dioxin-3,20-dione, melting point 255°–258°C, dec.

G.
9-Fluoro-11β-hydroxyandrost-4-eno[17β,16α-e][2,7,9]trioxabicyclo[3.3.1]nonane-3,4'-dione Following the procedure of Example 1G, but substituting 9-fluoro-2',3'-dihydro-11β,21-dihydroxypregn-4-eno[16α,17-b][1,4]dioxin-3,20-dione for 9-fluoro-2',b'-dihydro-11β,21-dihydroxy-5'-methylpregn-4-eno[16α,17-b][1,4]dioxin-3,20-dione, the title compound is obtained.

EXAMPLES 4 – 6

Following the procedure of Example 1 but substituting the steroid listed in column I for 9-fluoro-11β,16α,17,21-tetrahydroxypregn-4-ene-3,20-dione, 16,17-cycloborate, the steroid listed in column II is obtained.

| | Column I | Column II |
|---|---|---|
| 4. | 9-chloro-16α,17,21-trihydroxypregn-4-ene-3,11,20-trione, 16,17-cycloborate | 9-chloro-1'α-methylandrost-4-eno[17β,16α-e][2,7,9]trioxabicyclo[3.3.1]nonane-3,4',-11-trione |
| 5. | 9-bromo-6α-methyl-11β,-16α,17,21-tetrahydroxy-pregna-1,4-diene-3,20-dione,16,17-cycloborate | 9-bromo-11β-hydroxy-1'α,6α-dimethylandrosta-1,4-dieno-[17β,16α-e][2,7,9]trioxabicyclo[3.3.1]nonane-3,4'-dione |
| 6. | 2α-methyl-11β,16α,17,21-tetrahydroxypregn-4-ene-3,20-dione,16,17-cycloborate | 11β-hydroxy-1'α,2α-dimethyl-androst-4-eno[17β,16α-e]-[2,7,9]trioxabicyclo[3.3.1]-nonane-3,4'-dione |

EXAMPLES 7 – 9

Following the procedure of Example 2, but substituting the steroid listed in column I for 9-fluoro-11β,16α,17,21-tetrahydroxypregn-4-ene-3,20-dione,16,17-cycloborate, the steroid listed in column II is obtained.

| | Column I | Column II |
|---|---|---|
| 7. | 2,9-dichloro-11β,16α,17-21-tetrahydroxypregna-1,4-diene-3,20-dione-16,17-cycloborate | 2,9-dichloro-11β-hydroxy-1'α-phenylandrosta-1,4-dieno[17β,16-e][2,7,9]trioxabicyclo[3.3.1]-nonane-3,4'-dione |
| 8. | 6α,9-difluoro-11β,16α,17,-21-tetrahydroxypregn-4-ene-3,20-dione,16,17-cycloborate | 6α,9-difluoro-11β-hydroxy-1'α-phenylandrost-4-eno-[17β,16α-e][2,7,9]trioxabicyclo[3.3.1]nonane-3,4'-dione |
| 9. | 11β,16α,17,21-tetrahydroxy-pregna-1,4-diene-3,20-dione, 16,17-cycloborate | 11β-hydroxy-1'α-phenylandrosta-1,4-dieno[17β,16α-e][2,7,9]trio bicyclo[3.3.1]nonane-3,4'-dione |

What is claimed is:
1. A steroid having the formula

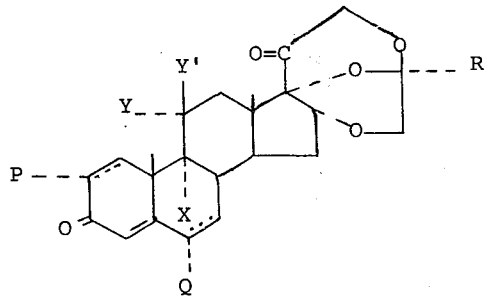

wherein P is hydrogen, methyl or chloro; Q is hydrogen, methyl or fluoro; X is hydrogen or halogen; Y is hydrogen and Y' is hydroxyl, or together Y and Y' are =O; and R is hydrogen, alkyl or aryl.

2. A steroid in accordance with claim 1 wherein R is hydrogen.

3. A steroid in accordance with claim 1 wherein R is alkyl.

4. A steroid in accordance with claim 3 wherein R is methyl.

5. A steroid in accordance with claim 1 wherein R is aryl.

6. A steroid in accordance with claim 5 wherein R is phenyl.

7. A steroid in accordance with claim 1 wherein Y is hydrogen and Y' is hydroxyl.

8. A steroid in accordance with claim 1 wherein X is halogen.

9. A steroid in accordance with claim 8 wherein X is fluoro.

10. A steroid in accordance with claim 1 wherein P and Q are each hydrogen.

11. A steroid in accordance with claim 1 wherein P and Q are each hydrogen; Y is hydrogen and Y' is hydroxyl; and X is fluoro.

12. The steroid in accordance with claim 11 having the name 9-fluoro-11β-hydroxy-1'α-methylandros-4-eno[17β,16α-e][2,7,9]trioxabicyclo[3.3.1]nonane-3,4'-dione.

13. The steroid in accordance with claim 11 having the name 9-fluoro-11β-hydroxy-1'α-phenylandrost-4-eno[17β,16α-e][2,7,9]trioxabicyclo[3.3.1]nonane-3,4'-dione.

* * * * *

UNITED STATES PATENT AND TRADEMARK OFFICE
CERTIFICATE OF CORRECTION

PATENT NO. : 3,945,997
DATED : March 23, 1976
INVENTOR(S) : Christopher M. Cimarusti It is certified that error appears in the above-identified patent and that said Letters Patent are hereby corrected as shown below:

Column 10, line 58, "phenylpregm" should read
-- phenylpregn --.

Column 10, line 64, "[16α,17-b],4]" should read
-- [16α,17-b][1,4] --.

Column 12, line 62, "A-fluoro-" should read
-- A slurry --.

Column 14, example 7, Column II, "[17β,16" should read
-- [17β,16α --.

Column 14, example 9, Column II, "[2,7,9]trio" should read
-- [2,7,9]trioxa --.

Column 14, line 59, "methylandros" should read
-- methylandrost --.

*Signed and Sealed this* twenty-ninth Day of June 1976

[SEAL]

Attest:

RUTH C. MASON
*Attesting Officer*

C. MARSHALL DANN
*Commissioner of Patents and Trademarks*